(12) United States Patent
Leitch

(10) Patent No.: US 6,892,881 B2
(45) Date of Patent: May 17, 2005

(54) HOLDING DEVICE FOR USE WITH CATHETER PACKAGING

(75) Inventor: Shawn P. Leitch, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 439 days.

(21) Appl. No.: 09/731,521

(22) Filed: Dec. 6, 2000

(65) Prior Publication Data

US 2002/0066685 A1 Jun. 6, 2002

(51) Int. Cl.$^7$ .............................................. B65D 83/10
(52) U.S. Cl. ............................................. 206/364; 206/479
(58) Field of Search ................................ 206/364, 479, 206/478, 483, 460, 775, 495

(56) References Cited

U.S. PATENT DOCUMENTS

| | | | | |
|---|---|---|---|---|
| 2,254,431 A | * | 9/1941 | Levine ........................ 312/201 |
| 3,411,620 A | | 11/1968 | Steinbock .................. 206/63.2 |
| 3,460,742 A | | 8/1969 | Langdon ....................... 229/62 |
| 3,556,294 A | | 1/1971 | Walck, III et al. ......... 206/63.2 |
| 3,612,038 A | | 10/1971 | Halligan ................. 128/2.05 R |
| 3,633,758 A | | 1/1972 | Morse et al. .................. 211/13 |
| 3,677,250 A | | 7/1972 | Thomas |
| 3,750,875 A | | 8/1973 | Juster ..................... 206/63.2 R |
| 3,930,580 A | | 1/1976 | Bazell et al. ................ 206/439 |
| 3,967,726 A | * | 7/1976 | Roeser ........................ 206/306 |
| 3,967,728 A | | 7/1976 | Gordon et al. .............. 206/364 |
| 4,154,339 A | * | 5/1979 | Dutra ........................ 206/315.1 |
| 4,262,800 A | * | 4/1981 | Nethercutt ................... 206/364 |
| 4,306,656 A | | 12/1981 | Dahlem ....................... 206/390 |
| 4,367,816 A | | 1/1983 | Wilkes ........................ 206/439 |
| 4,563,177 A | | 1/1986 | Kamen |
| 4,583,641 A | * | 4/1986 | Gelzer ........................ 206/479 |
| 4,936,464 A | | 6/1990 | Kim |
| 5,029,702 A | * | 7/1991 | Tong ........................ 206/315.1 |
| 5,105,942 A | | 4/1992 | van Veen et al. ........... 206/364 |
| 5,131,537 A | | 7/1992 | Gonzalez ..................... 206/364 |
| 5,165,540 A | | 11/1992 | Forney ........................ 206/364 |
| 5,234,106 A | * | 8/1993 | Transue et al. ............. 206/363 |
| 5,392,918 A | | 2/1995 | Harrison ..................... 206/571 |
| 5,447,231 A | | 9/1995 | Kastenhofer ................ 206/364 |
| 5,467,873 A | | 11/1995 | Kastenhofer ................ 206/363 |
| 5,497,601 A | | 3/1996 | Gonzalez ..................... 53/449 |
| 5,501,341 A | | 3/1996 | Van Es ........................ 206/364 |
| 5,848,691 A | | 12/1998 | Morris et al. ............... 206/364 |
| 5,895,374 A | * | 4/1999 | Rodsten ...................... 604/163 |
| 5,947,296 A | | 9/1999 | Castora ....................... 206/571 |
| 6,009,998 A | | 1/2000 | Webinger ................... 206/364 |
| 6,053,313 A | | 4/2000 | Farrell et al. ............... 206/364 |
| 6,068,121 A | | 5/2000 | McGlinch ................... 206/364 |
| 6,074,368 A | | 6/2000 | Wright ........................ 604/179 |
| 6,090,076 A | | 7/2000 | Lane, Jr. |

FOREIGN PATENT DOCUMENTS

| | | |
|---|---|---|
| EP | 0 423 855 B1 | 4/1991 |
| EP | 0 440 427 B1 | 8/1991 |
| EP | 0 602 965 A2 | 6/1994 |
| EP | 0 667 170 A1 | 8/1995 |

* cited by examiner

Primary Examiner—Mickey Yu
Assistant Examiner—Troy Arnold
(74) Attorney, Agent, or Firm—Crompton, Seager & Tufte, LLC

(57) ABSTRACT

A packaging system for an elongate medical device includes a sheet of material which defines a generally planar surface for receiving the elongated medical device thereon. A plurality of butterfly tabs are adhesively attached to the planar surface at selected locations to retain the medical device in position. The butterfly tabs eliminate weaving of catheters onto mounting cards having tabs punched therethrough. The butterfly tabs preferably include at least two adhesive-coated wing portions connected by a linking portion that overlies the medical device and is preferably free of adhesive.

10 Claims, 2 Drawing Sheets

Fig. 4
Fig. 5
Fig. 6
Fig. 7
Fig. 8
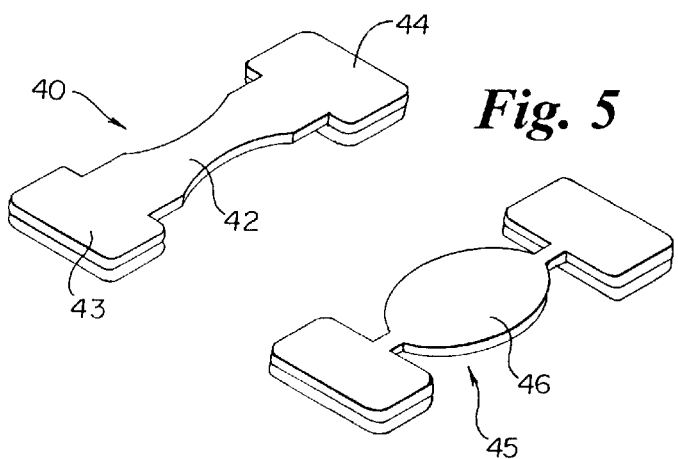
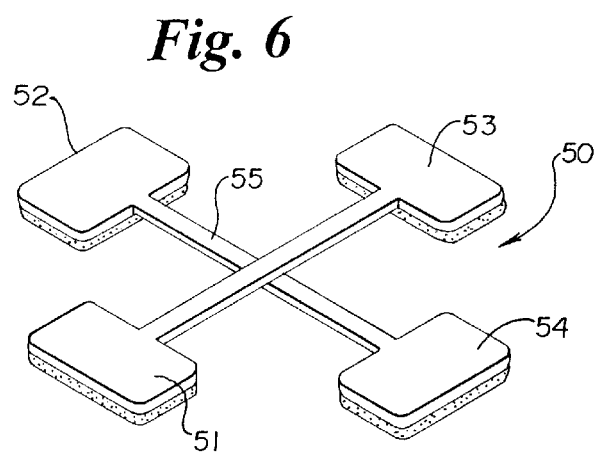
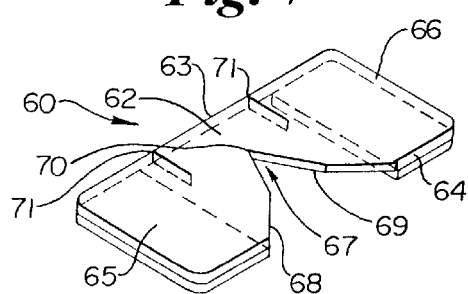
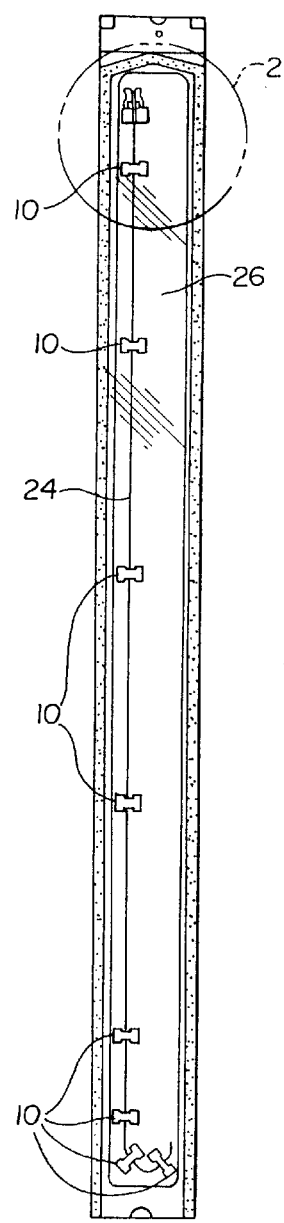

HOLDING DEVICE FOR USE WITH CATHETER PACKAGING

TECHNICAL FIELD

The present invention generally relates to the field of medical device packaging, and more specifically to the field of packaging catheters and other similar medical devices in a manner that maintains the catheter's desired shape, position and sterility within the packaging during sterilization, shipment and storage. The present invention further relates to improved packaging materials and methods for packaging catheters, wherein the improvements allow easy, damage-free removal of the medical devices from their packaging.

BACKGROUND OF THE INVENTION

Numerous medical procedures require the advancement and positioning of medical devices within body lumens. Intravascular catheters, in particular, are currently utilized in a wide variety of minimally invasive medical procedures. Generally, an intravascular catheter enables a physician to remotely perform a medical procedure by inserting the catheter into the vascular system of the patient at a location that is easily accessible, and thereafter, navigating the catheter to a desirable target site. Using this method, virtually any target site in a patient's vascular system may be remotely accessed, including the coronary, cerebral, and peripheral vasculature.

Typically, the catheter enters the patient's vasculature at a convenient location, such as a blood vessel in the neck or near the groin. Once the distal portion of the catheter has entered the patient's vascular system, the physician may urge the distal tip forward by applying longitudinal forces to the proximal portion of the catheter. For the catheter to effectively communicate these longitudinal forces, it is desirable that the catheter have a high level of pushability and kink resistance.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that the intravascular catheter be very flexible, particularly in the distal portion.

While advancing the catheter through the tortuous path of the patient's vasculature, physicians often apply torsional forces to the proximal portion of the catheter to aid in steering the catheter. To facilitate the steering process, the distal portion of the catheter may include a plurality of bends or curves. Torsional forces applied on the proximal end must translate to the distal end to aid in steering. It is, therefore, desirable that the proximal portion of the intravascular catheter has a relatively high level of torqueability and rigidity to facilitate steering.

The distance between the access site and the target site is often in excess of 100 cm. The inside diameter of the vasculature at the access site is often less than 5 mm. In light of the geometry of the patient's body, it is desirable to combine the features of torqueability, pushability, and flexibility into a catheter that is relatively long and has a relatively small diameter.

The physical attributes that aid a physician in advancing the catheter through the tortuous path of the patient's vasculature also create packaging difficulties for the manufacturer. For a catheter to be used in the manner for which it is manufactured, the shape of the catheter must be maintained in its original form. Therefore, the proximal portion of the catheter body needs to be maintained in a generally straight alignment. The unique distal end formations, on the other hand, must be secured in the shape that the manufacturer originally imparts. As a result, a catheter's packaging is generally long and narrow.

Current packaging techniques for catheters generally include the use of a mounting card. Mounting cards are generally long, stiff cards having a plurality of die-cut tabs that hold the catheter in place. These die-cut tabs are usually created using a manual press that cuts the specific shape of the tab into the mounting card. Once the tabs are cut, the tabs are then raised, allowing the catheter to be woven under the tabs. The tabs are then lowered, allowing the catheter to be held in place by the tab's downward pressure. One in the art generally knows this weaving procedure as "webbing."

Because the press physically cuts into the mounting card when forming the tab, residual foreign material is often released when the tabs are raised for the webbing process. This residual foreign material is commonly known as "angel hair." It is desirable to minimize all foreign material when packaging medical devices. Current packaging standards, however, permit the presence of some foreign material.

Acceptable foreign material is generally smaller than five square millimeters in size and no more than three pieces are permitted per unit packaged. These small pieces of foreign material, however, are known to attach themselves to the packaged catheter. Complications are foreseeable from this contamination of the packaged catheter. For example, while inserting the catheter within a bodily pathway, the foreign material may also be introduced within the body.

Once the catheter is webbed onto the mounting card, the device is secured. The downward force exerted by the tabs prevents lateral and longitudinal movement of the catheter. Although this is quite beneficial in maintaining the catheter's desired shape and position within the packaging, it is less desirable with regards to the removal of the catheter from its packaging.

Physicians have found that catheters fastened by tabs often succumb to physical deformation during the catheter's removal. The tabs are so effective at securing the catheter that, even when the physician carefully removes the catheter, the catheter occasionally deforms. The deformation is particularly prevalent in the highly modified distal end region of the catheter. Because the distal end is generally the most flexible region of the catheter, the distal end may be deformed quite readily. Pulling the device through a tab may easily impart a new structural formation to the catheter that was not desired by the manufacturer. Thus, the manufacturer's precision in manufacturing the distal end region can be easily frustrated by the tabs.

A similar deformation issue associated with the removal of the catheter from tabs is kinking. Because the tabs are formed from the same rigid material as the mounting card, the tabs also possess a significant level of rigidity. This rigidity aids the tabs in securing the catheter under its downward pressure. When a physician, however, pulls on the catheter to free the device from the confines of the tab, a permanent kink or bend may be imparted to the catheter. Release of the catheter from the mounting card is generally achieved by force. Ideally, the tabs will yield to the force exerted upon the catheter and allow the catheter to be removed. In certain circumstances, however, it is the catheter that yields to the rigidity of the tab. The incidence of this occurring is particularly high when a physician pulls upon the catheter perpendicular to the mounting card while it is secured onto the mounting card. When pulled as such, the catheter yields to the tab and bends at a sharp angle near the edge of the tab. Catheters possessing such sharp bends lose much of their pushability strength because of the natural tendency to bend at these weakened points. This compromise in the catheter's configuration renders the catheter useless for its desired intention.

Webbing catheters onto their mounting cards is an arduous process. This process is made more difficult by the size and geometry of most catheters. As a result, automation of the webbing process has proven to be a daunting task.

The webbing process utilizes a flat plate press commonly known as a "webber." The plate of the webber machine is slightly longer than the mounting card (approximately 40 inches long) and approximately six (6) inches deep. The webber is further described as having an upper and lower plate hinged at the back with a handle located in the middle front of the press. From a seated position, the assembler lifts the handle, requiring a lift and push force from the elbow and shoulder. The weight of the upper plate of the press weighs approximately 5 pounds. With an extended arm, however, the force required to lower and raise the plate equates to about 40 pounds. The assembler weaves the catheter onto the mounting card using a slight back and forth motion powered by the shoulder muscles. Currently, upwards of thirty (30) repetitions of arm movements (including raising and lowering the plate, weaving the catheter through the die-cut tabs, inserting and removing the cardboard) are completed every minute, assuming a cycle time of ten (10) seconds. The process thus has the potential for over-exertion and injury.

SUMMARY OF THE INVENTION

The present invention provides a packaging design and method of manufacture that maintains a medical device's desired shape, position and sterility within its packaging during sterilization, shipment and storage, while permitting easy removal from the same when desired. This invention is preferably achieved using a series of "butterfly" shaped adhesive tabs.

Butterfly tabs are manufactured independent of the mounting card. Because butterfly tabs are formed independent of the mounting card, contamination of the packaging by foreign material, such as angel hair, is substantially reduced. Butterfly tabs may be die-cut (similar to the tabs on the mounting card), however, since the production of butterfly tabs are a separate phase of the packaging process, the butterfly tabs may undergo a separate inspection for loose foreign material.

In a preferred embodiment, the butterfly tabs are selectively coated over a portion of their surface with an adhesive. Those portions possessing the adhesive readily adhere to a mounting card, or other suitable surface. In one embodiment, the "winged" portions of the butterfly tab possess the adhesive coating. In contrast, the portion of the butterfly tab that links the winged portions generally lacks any adhesive. This "linking" portion of the butterfly tab restrains the medical device by a downward force created by outstretching the butterfly tab over the medical device. Because the linking portion lies over the medical device, the butterfly tab permits release through tearing, breaking or fissure of the linking portion of the butterfly tab.

Tearing of the linking portion may be aided through design. The tearing release of the butterfly tab allows a physician to remove a medical device from its packaging with minimal effort. The sensitivity of the linking portion must therefore be carefully balanced to maintain the medical device's shape and position while permitting easy removal. In certain embodiments, the physician releases the medical device through a slight vertical or horizontal pull on the medical device. Such minimal effort reduces deformations formed by kinking. Because the linking portion is designed to yield to the medical device during release, deformation caused by the rigidity of the tab is eliminated. Similarly, the distal end portion of a catheter is significantly less likely to deform from a readily torn butterfly tab.

In one embodiment, a manufactured preferential tear line is imparted onto the linking portion of the butterfly tab. In additional embodiments, segments of the linking portion are constructed of a relatively thin piece of material, permitting the selected horizontal or vertical force to cause the linking portion to tear.

As described earlier, the butterfly tabs are formed independently of the mounting card. Therefore, in a preferred embodiment, the butterfly tabs may be constructed using off-the-shelf equipment. Such equipment is modifiable to be incorporated into a fully automated packaging system.

A major factor in the failure to fully automate the packaging process to date has been the need for assemblers to weave the medical devices, and more specifically catheters, under the raised tabs of the mounting card. There is thus a need for the present invention which includes the use of a butterfly tab, and the automation potential it affords by eliminating the weaving process.

BRIEF DESCRIPTION OF THE DRAWINGS

FIG. 4 is a perspective view of a butterfly tab having a linking portion that tapers inward from the ends of the linking portion to a reduced point at the center of the linking portion;

FIG. 5 is a perspective view of a butterfly tab having a linking portion that tapers inwardly from the center of the linking portion to a reduced point at the ends of the linking portion;

FIG. 6 is a perspective view of a butterfly tab having multiple opposing winged portions that are interconnected by at least one linking portion;

FIG. 7 is a perspective view of a butterfly tab having a linking portion that incorporates a tapered channel on one side and a line of weakness radiating from the apex of the tapered channel on the other side; and FIG. 8 is a plan view of a mounting card having a plurality of butterfly tabs disposed thereon for securing a medical device for packaging, the mounting card further disposed within a sterile pouch for shipment and storage.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes are provided for selected elements. Those skilled in the art will recognize that many of the examples provided have suitable alternatives that may be utilized.

Prior art mounting cards are generally made from a solid, bleached sulfate board having a thickness of approximately 0.005 to 0.020 inches. However, the material and construction of the mounting card is not critical to the present invention and may vary widely from embodiments described herein. For example, other suitable materials for a mounting card include high-density polyethylene (HDPE), Mylar, Tyvek, polyethylene, and polyester. Such materials possess sufficient rigidity to withstand significant bending along the length of the mounting card.

Generally, mounting cards are approximately 100 to 125 cm in length. The length of the mounting card varies with the length of the medical device. Accordingly, it is conceivable that mounting cards are desired as small as, for example, 40 cm in length and as long as, for example, 175 cm in length. The width of the mounting card is similarly contingent upon the type of medical device being packaged. Generally, however, the width of the mounting card is approximately 4 to 13 cm.

According to conventional methods, the shaft portion of the catheter is secured to the mounting card using a plurality of die-cut tabs. The die-cut tabs are generally created using a press that cuts the desired shape of the tab into the mounting card. The die-cut tabs can be semicircles having a base and an arc. The die-cutting machine cuts the outline of the arc of the tab through the mounting card. The base is uncut by the machine and acts as a hinge, allowing the arc portion of the tab to be raised vertically from the plane of the mounting card.

Once the tabs are cut, the tabs are then raised allowing an assembler to weave the catheter under the raised tabs. Because the tabs are formed from the rigid mounting card material, the tabs are naturally biased to be in same plane as the mounting card. This creates a significant downward pressure exerted at the base of the die-cut tab when raised. The tabs are then lowered on the catheter shaft, holding the catheter shaft by this natural downward pressure. One in the art generally knows the above-described weaving procedure as "webbing".

Figure 1:
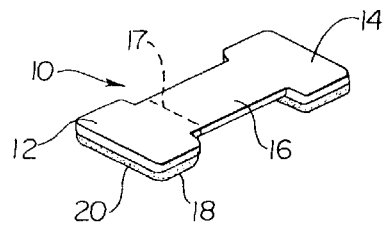
FIG. 1 is a perspective view of a butterfly tab having a preferential tear line imparted onto the linking portion of the tab.

Now referring to FIG. 1, a perspective view of a butterfly tab 10 having a preferential tear line imparted onto a linking portion of the tab is depicted as one preferred embodiment of the present invention. The butterfly tab 10 is characterized by two "winged" portions 12,14 interconnected by a "linking" portion 16. The winged portions are approximately 0.125 to 1.5 inches in length by 0.125 to 0.75 inches in width. The dimensions of individual winged portions 12,14 may vary, however, depending upon the desired application. A winged portion for use in retaining a catheter shaft preferably has length and width dimensions of 0.5 inch by 0.25 inch. A winged portion for using in retaining a hub assembly, in contrast, preferably has length and width dimensions of 1.0 inch by 0.50 inch. Although the winged portions 12,14 are depicted in FIGS. 1–7 as generally rectangular in shape, the winged portions 12,14 may take on other geometric shapes without departing from the scope of the invention. Examples of other suitable geometric shapes include a square, a circle, an oval, an ellipse, a parallelogram, or a diamond-type shape.

The underside or backside 18 of the winged portions of the butterfly tab 10 is selectively coated with an adhesive 20. The adhesive 20 is generally characterized as one capable of forming a tight bond with common packaging material. As such, the adhesive 20 must be capable of readily bonding with at least one of the following packaging materials: solid bleach sulfate board, high density polyethylene, Mylar, Tyvek, polyethylene, and polyester. The adhesive is additionally characterized as being capable of forming a sufficient bond when exposed to common sterilization processes. The adhesive 20 should, therefore, retain a fixed position when exposed to gas (particularly ethylene oxide), heat, and pressure.

Figure 2:
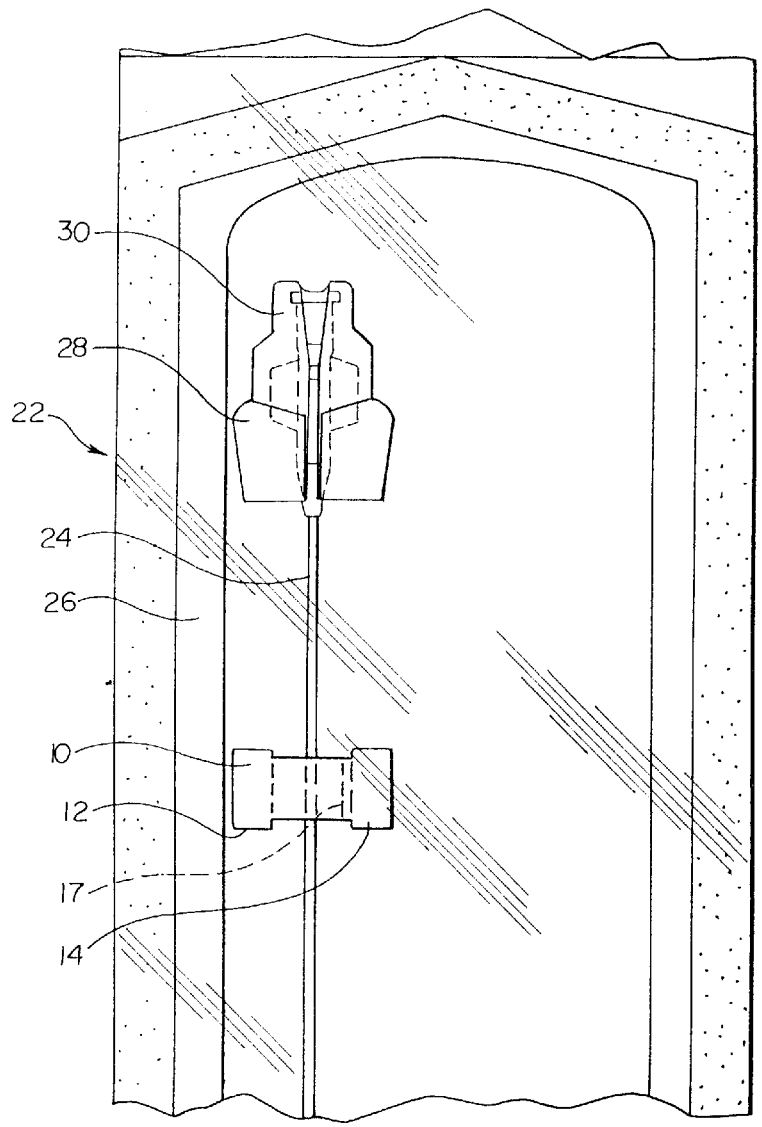
FIG. 2 is a partial plan view of a mounting card, the mounting card including die-cut tabs for securing a medical device and a butterfly tab of the present invention.

The "linking" portion 16 of the butterfly tab 10 is the portion of the butterfly tab 10 that actually physically restrains movement of the medical device in use. A downward force created by outstretching of the linking portion 16 of the butterfly tab 10 over the medical device restrains movement of the medical device. As such, restraint of the medical device by the butterfly tab 10 is preferably a product of friction. Referring to FIG. 2, a partial plan view of a portion of a catheter package 22 with a catheter 24 mounted therein is shown. The Figure depicts the use of butterfly tab 10 to hold the catheter 24 shaft in position on a mounting card 26. The Figure also depicts a conventional tab 28 which has been cut into the mounting card 26 to retain the hub 30 of the catheter 24. Thus, this is within the scope of the present invention to utilize the butterfly tab embodiments in conjunction with tabs cut into the mounting card. In particular, the single tab at the location of the hub 30 could be preformed into the mounting card as the location of such single tab could be utilized for many catheter designs as it will always position the proximal end of the catheter and will not be dependent upon the length and shape of the particular catheter.

As depicted in FIG. 2, the butterfly tab end has wing portions 12 and 14 adhesively bound to the mounting card 26 while the linking portion 16 extends over the catheter shaft 24 and frictionally holds such shaft in place. For the embodiment of FIG. 1 and that which is utilized in FIG. 2, a preferential tear line 17 is included across the linking portion 16 to allow removal of the catheter shaft by tearing along such line of weakness.

Linking portion 16 preferably lack adhesive material. It is generally believed that the medical device should be free from any contact with adhesive material. Further embodiments utilizing adhesives are conceivable, however. For example, one side of the linking portion 16 may have a pressure sensitive adhesive (PSA) applied thereto. In this embodiment, the adhesive material is biocompatible or biologically inert. Such an adhesive provides additional restraint to the above-mentioned frictional forces vis-à-vis the adhesive bond between the linking portion and the medical device. The use of PSAs is preferred because these materials are selectively adherent. When desired, the PSA releases its bond, allowing an object to be released. PSAs also generally do not transfer to the object they are adhering (i.e., they can be cleanly removed from an adherent). As such, very little adhesive, if any, will be transmitted to the medical device after release from a PSA-coated linking portion.

The linking portion 16 generally controls the release of the medical device from the restraint by the butterfly tab. Release is generally accomplished through fissure or tearing of the linking portion 16 of the butterfly tab 10. The fissure release of the butterfly tab 10 allows a physician to remove a medical device from its packaging with minimal effort.

The physician generally releases the medical device using a slight vertical or horizontal pull on the medical device.

Because the liking portion can be designed to tear at a desired amount of force for a particular device or portion of a device, deformations formed by kinking are greatly reduced. The fissure sensitivity of the linking portion, however, must be carefully balanced to maintain the medical device's shape and position while permitting easy removal. Fissure sensitivity of the linking portion may be balanced and aided through design. Design modifications are focused primarily on the shape, material and fissure aids, specifically tailored for the linking portion.

The shape of the linking portion may be designed to enhance fissure. In FIG. 1, the butterfly tab 10 is generally rectangular in shape. The linking portions taper inward slightly as they extend from the winged portions of the butterfly tab. Such tapering is not necessary, but is believed to enhance performance. The length of the linking portion varies according to the device being restrained upon a mounting card. The length of each linking portion may additionally vary on the same device, depending upon the placement of the particular butterfly tab of which it is a part. For example, the length of a linking portion restraining a hub assembly of a catheter is significantly larger than the length of the linking portion restraining the distal end of the same catheter. The linking portions are approximately 0.125 to 1.5 inches in length by 0.0313 to 1.0 inches in width. A linking portion for a catheter shaft preferably has length and width dimensions of 0.5 inch by 0.25 inch. Whereas, a linking portion for a hub assembly preferably has length and width dimensions of 1.0 inch by 0.50 inch.

Materials suitable for the linking portion include any paper or film of such thickness capable of yielding to a medical device when a suitable force which does not cause kinking or deformation of the medical device is exerted upon the material. In certain embodiments, it is envisioned that certain segments of the linking portion are constructed of such thin material that the suitable horizontal or vertical force causes the linking portion to fissure. A preferred material permitting fissure in the linking portion is polystyrene.

Alternatively, the material forming the linking portion may be of a greater thickness, but additionally including a preferential tear line imparted thereto to aid in the material's fissure. Although the linking portion will generally tear along the preferential tear line, it need not according to the invention.

FIG. 1 shows a manufactured preferential tear line 17 imparted along the width of the linking portion 16, in the middle of the linking portion's length. In the embodiment of FIG. 1, preferential tear line 17 is comprised of a plurality of perforations. Other embodiments of perforations are possible without deviating from the spirit and scope of the present invention. For example, perforations may comprise single or multiple holes, slots, slits, or dimples. Likewise, other embodiments of preferential tear line 17 are possible without deviating from the spirit and scope of the present invention. For example, preferential tear line 17 may comprise a groove, a fold, or any other general line of weakness imparted in the linking portion to aid in fissure.

In further embodiments, it is envisioned that the preferential tear line 17 may be set off center. These embodiments include imparting a preferential tear line to the linking portion where the winged portion engages the linking portion. Additionally, the preferential tear line may be imparted at any location along the length of the linking portion between the center of the linking portion and the edge of the linking portion where the linking portion engages the winged portion of the butterfly tab. A yet further embodiment includes imparting a plurality of preferential tear lines along the length, the width or both of the linking portion of the butterfly tab.

Figure 3:
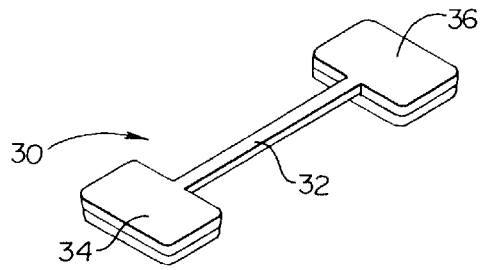
FIG. 3 is a perspective view of a butterfly tab having a linking portion constructed of tab material possessing a thin width.

FIG. 3 shows a perspective view of an alternative butterfly tab 30 having a linking portion 32 constructed of material possessing a thin width. The linking portion 32 extends between adhesive coated wings 34,36. The linking portion 32 of FIG. 3 is comprised of a paper or film having a width between 0.0156 and 0.125 inches. The tab is used as described with reference to FIGS. 1 and 2. In preferred embodiments, butterfly tabs having linking portions of such dimensions are positioned over delicate regions of a medical device. In particular, such linking portions are best suited for the bends and curves of the distal-most regions of a catheter. It is well within the scope of this embodiment, however, to use the above-described linking portions in connection with the proximal portions of a catheter shaft, as well as a hub assembly.

A physician releases a medical device secured by a thin-width linking portion by applying a gentle vertical or horizontal pull on the medical device. This pull subsequently causes the thin-width linking portion to fissure. Fissure generally occurs where the linking portion attaches to the winged portions of the butterfly tab. The resulting fissure of the thin-width linking portion thereby liberates the medical device from the butterfly tab and the mounting card.

When using materials of greater thickness for the thin-width linking portion of FIG. 3, fissure may be aided by imparting a preferential tear line to the material. In preferred embodiments, at least one preferential tear line is imparted proximate where the linking portion attaches to the winged portions of the butterfly tab.

FIG. 4 shows a perspective view of an alternative butterfly tab 40 having a linking portion 42 that tapers inward from the ends of the linking portion 42 to a reduced width at the center of the linking portion 42. The shape of this embodiment is designed for aiding in linking portion fissure. As with prior embodiments, the linking portion 42 extends between adhesive coated winged portions 43,44.

When a physician gently pulls on the medical device secured by the dual taper linking portion, the natural tendency is for the medical device to move toward the apex of the inverted semi-circle. Thus, if a catheter were positioned slightly off center when secured by the dual taper linking portion, when pulled, the catheter would shift to the center of the dual taper design. In effect, the catheter would follow the arc formed by the dual taper linking portion until reaching the apex, or center, of the inverted semi-circle. The center of the dual taper linking portion is additionally the narrowest section, width-wise, of the linking portion. By design, this section is also the easiest to tear. Therefore, the linking portion design illustrated in FIG. 4 is two-fold; first, the shape of the butterfly tab moves the catheter to the center of the linking portion, and second, the shape aids in fissure at the narrowest section of the linking portion.

In a further embodiment, the centermost section of the dual taper linking portion may possess a preferential tear line. Preferably, the preferential tear line runs along the width of the narrow section. In alternate embodiments, however, the preferential tear line may run lengthwise within the narrowest section of the dual taper design.

FIG. 5 shows a perspective view of an alternative butterfly tab 45 having a linking portion 46 that tapers inward from the center of the linking portion 46 to a reduced width at the ends of the linking portion. The linking portion 46 of FIG. 5 is significantly larger at the center than at the ends. The ends of the linking portion are preferably the narrowest points on the tab. As such, these are generally the sites where tearing will occur. In order to assist fissure at these sites, the manufacturer may impart a preferential tear line at these ends. In a preferred embodiment, the preferential tear lines run along the width of these narrow sections. In alternate embodiments, however, the preferential tear lines run lengthwise within the narrow sections of the linking portion.

The linking portion of FIG. 5 is functionally advantageous. This design provides greater surface contact between the linking portion of the butterfly tab and the medical device being restrained. Increased surface contact provides greater restraining power, preferably by increasing frictional forces between the tab and the medical device. When a physician gently pulls upon the medical device, the physician's applied force is more readily transmitted along the increased surface area of the above-described linking portion. The force applied by the physician will either cause the large center section of the linking portion to raise vertically, or shift horizontally, with either movement causing increased strain at the linking portion's narrow ends. The stress at the ends eventually causes one or both of the ends to fissure. The resulting fissure releases the medical device from the butterfly tab.

FIG. 6 shows a perspective view of an alternative butterfly tab 50 having multiple opposing winged portions 51, 52, 53, 54 that are interconnected by at least one linking portion 55. In one embodiment, the butterfly tab contains at least four (4) winged portions. The winged portions are generally arrayed in an "X-shaped" configuration. This configuration allows a medical device to extend longitudinally in-between the winged portions without physically obstructing the path of the device.

The linking portion of FIG. 6 can preferably be a single piece of paper or film that interconnects the winged portions of the butterfly tab. Alternatively, as shown in FIG. 6, this embodiment can be achieved using two properly arranged butterfly tabs, such as those depicted in FIG. 3. The linking portion 55 of this embodiment is best described as having a center and a plurality of struts that extend from the center and attach to their corresponding winged portions 51, 52, 53, 54. Each individual strut has a width between about or approximately 0.0156 and 0.125 inches.

In one embodiment, the width at the center of the linking portion is larger than the width of the corresponding struts. Preferably, the center is circular in shape. The larger center section provides greater surface contact between the linking portion of the butterfly tab and the medical device being restrained. Increased surface contact additionally provides greater restraining power by increasing the frictional force between the center section of the linking portion and the medical device. Therefore, since a larger segment of the medical device is in contact with the linking portion, specifically the center, significantly less effort is needed to fissure the butterfly tab.

Preferential line tears may be placed anywhere along the body of the struts, or alternatively, at the center of the linking portion. In one embodiment, the preferential line tears are positioned where the struts join the center section of the butterfly tab. In an alternate embodiment, the preferential line tears may be placed where the struts engage the adhesively bound winged portions of the butterfly tab.

In a further embodiment, more than one linking portion is used to form the butterfly tab. Each individual linking portion connects opposing winged portions. The center of the tab, therefore, contains at least two superposed layers of linking portions.

In preferred embodiments, the butterfly tabs having multiple linking portions herein described are best suited for the proximal portions of a catheter shaft and the hub assembly. It is well within the scope of this embodiment, however, to use the above-described linking portion in connection with the delicate regions of a medical device. In particular, such linking portions are also suitable for the bends and curves of the distal-most regions of a catheter.

A physician releases a medical device secured by the above-described linking portion by applying a vertical or horizontal pull on the medical device. This pull subsequently causes either the struts or the center section to fissure, if not both. Fissure, however, generally occurs where the struts attach to the winged portions of the butterfly tab. The resulting fissure of the struts or center section thereby releases the medical device from the butterfly tab and the mounting card.

FIG. 7 shows a perspective view of an alternative butterfly tab 60 having a linking portion 62 that tapers to form a channel 67. As with the other above-described embodiments, linking portion 62 extends between adhesive coated winged portions 65 and 66. Linking portion 62, in contrast to the other embodiments, possesses two distinct side regions: a first side region 63 and a second side region 64. First side region 63 is generally flush with the sides of winged portions 65 and 66. As such, first side region 64 extends between the two sides of winged portions 63 and 64 without noticeable deviation. Second side region 64, on the other hand, forms channel 67 within linking portion 62.

Second side region 64 preferably undergoes at least one, and more preferably two taperings to form channel 67. In one embodiment, first tapering 68 immediately extends inwardly from both winged portions 65 and 66. More specifically, first tapering 68 extends inwardly at angle of approximately 40 to 50 degrees in pitch. Second tapering 69 subsequently increases the pitch of first tapering 68 at a distance approximately one quarter through the body of linking portion 62. Second tapering 69 generally extends inwardly at a pitch of approximately 60 degrees. The pitch of second tapering 69, from both ends, terminates at the channel's apex 70 within linking portion 62. In a preferred embodiment, the apex of channel 70 is approximately one half through to just proximate the first side region 63 of linking portion 62. The resulting channel 67 is thereby defined by these series of successive taperings 68 and 69 ending at apex 70.

The shape of this embodiment is designed for aiding in the fissure of linking portion 62. When a physician gently pulls on the medical device secured by two-sided linking portion 60, the natural tendency is for the medical device to move toward and into the center of channel 67. The pitch of first tapering 68 creates an expansive opening into the entrance of channel 67. This expansive opening permits a catheter that is positioned slightly off center under the two-sided linking portion 60, when pulled, to shift to the center of channel 67. From within channel 67, moderate pulling pressure results in the fissuring of the remaining linking portion 62 from the apex of the channel 70 through to first side region 63. In a further embodiment, a preferential tear line may be incorporated within linking portion 62 to aid in fissure. Preferably, the preferential tear line extends from the apex of channel 70 to first side region 63.

Relief slits 71 may be placed parallel to the direction of the secured medical device to add flexibility. As indicated in FIG. 7, two relief slits 71 are included on first side region 63 with the linking portion 62 on both sides of the channel 67. Relief slits 71 are particularly useful in securing medical devices possessing an oval or round outer profile. Although not specifically discussed, the use of relief slits may additionally be suitable in applications using earlier-discussed embodiments.

FIG. 8 shows a plan view of a mounting card 26 having a plurality of butterfly tabs 10 disposed thereon for securing a medical device 24 for packaging. Although only one medical device 24 is specifically illustrated, the present invention is additionally applicable for mounting cards 26 securing more than one medical device 24 thereon. The butterfly tabs 10 are positioned along the length of the medical device to restrain the device from shifting during packaging, sterilization, shipment and storage. The number, shape, and size of butterfly tabs used may be varied depending upon the desired application.

As described in detail above, the butterfly tabs are formed independent of the mounting card. Butterfly tabs are generally constructed of a separate paper or film material. Several advantages arise from using an independent source for securing the medical device. First, because the securing means is not an outgrowth of the mounting card, the mounting card is no longer the only product the medical device may be secured upon. For example, the butterfly tabs may secure a medical device to a piece of Mylar or other film material. Thus, the final package may be a bag having no rigid support member. Alternatively, the butterfly labels may be attached to a rigid support member not suitable for forming die-cut tabs.

Second, because the butterfly tabs are formed independent of the mounting card, contamination caused by angel hair can be entirely eliminated. In a preferred embodiment, the butterfly tabs are constructed using off-the-shelf labeling equipment. Such equipment is modifiable to be incorporated into a fully automated packaging system.

Since webbing is a laborious process, automation of the process is desirable. A major factor in the failure to fully automate the packaging process to date has been the need for assemblers to weave the medical devices, and more specifically catheters, under the raised tabs of the mounting card. Automation removes these costs from production.

In a preferred embodiment, an operator would place a catheter onto a mounting card, or the equivalent thereto. A guide mechanism would then position the catheter into the catheter's desired alignment. The labeling portion of the machine would then selectively apply butterfly tabs over, and along the length of, the catheter shaft. The applied butterfly tabs may then be wiped to remove excess adhesive, if deemed necessary. Next, the catheter and the mounting card are then fed into a package-sealing device or placed into a pre-manufactured packaging pouch. In one embodiment, the mounting card and catheter are inserted into a Tyvek bottom, Mylar top, pouch. The package-sealing device seals the mounting card securely within the pouch. Finally, the pouch is labeled, sterilized (if not done prior), and packaged for shipment.

Having thus described the preferred embodiments of the present invention, those of skill in the art will readily appreciate that yet other embodiments may be made and used within the scope of the claims hereto attached.

What is claimed is:

1. A combined elongate medical device and package comprising:
   a mounting card defining a generally planar surface;
   an elongate medical device overlying a portion of the generally planar surface of the mounting card; and
   a plurality of butterfly tabs, each including at least two winged portions having an adhesive coated on at least a portion thereof adhered at selected locations on the generally planar surface of the mounting card and extending over the elongate medical device to retain the medical device in position on the generally planar surface, wherein each butterfly tab includes a linking portion connecting the winged portions, wherein the linking portion is designed to yield to an applied force; and wherein the linking portion possesses a preferential tear line.

2. The combined elongate medical device and package of claim 1, wherein the linking portion does not have an adhesive coating.

3. The combined elongate medical device and package of claim 1, wherein the linking portion has a central narrowed width portion which provides a weakened area for tearing.

4. The combined elongate medical device and package of claim 1, wherein the linking portion has a broad central portion and narrow end portions near the adhesive-coated winged portions.

5. The combined elongate medical device and package of claim 1, wherein the butterfly tabs include at least one butterfly tab having at least four adhesive-coated winged portions connected by at least two linking portions.

6. A method for packaging elongate medical devices comprising the steps of:
   providing a mounting card defining a generally planar surface;
   providing an elongated medical device;
   positioning the elongate medical device on a portion of the planar surface of the mounting card;
   providing a plurality of butterfly tabs, the tabs having a surface including an adhesive coated on at least a portion thereof and a linking portion designed to yield to an applied force; wherein the linking portion possesses a preferential tear line; and
   adhering the plurality of butterfly tabs at selected locations on the planar surface of the mounting card such that the butterfly tabs overlay the elongated medical device at the selected locations and retain the elongated medical device in position on the generally planar surface.

7. The method of claim 6, wherein the mounting card includes a tab formed through the planar surface and the elongated medical device includes a hub portion wherein the elongated medical device is positioned such that the tab retains the hub portion in position prior to adhering the plurality of butterfly tabs.

8. The method of claim 6, further comprising the step of positioning the mounted elongate medical device and mounting card in a polymeric package.

9. The method of claim 8, further comprising the step of sterilizing the packaged elongate medical device as mounted on the mounting card and placed in the polymeric package.

10. The packaging system of claim 1, wherein the linking portion does not have an adhesive coating.

* * * * *

UNITED STATES PATENT AND TRADEMARK OFFICE
CERTIFICATE OF CORRECTION

PATENT NO. : 6,892,881 B2
DATED : May 17, 2005
INVENTOR(S) : Shawn P. Leitch

It is certified that error appears in the above-identified patent and that said Letters Patent is hereby corrected as shown below:

Column 12,
Line 5, delete "overlying a portion of", and insert therefor -- positioned on --.
Line 37, delete "a portion of".

Signed and Sealed this

Second Day of August, 2005

JON W. DUDAS
*Director of the United States Patent and Trademark Office*